United States Patent [19]

Seamone et al.

[11] Patent Number: 4,604,098

[45] Date of Patent: Aug. 5, 1986

[54] PROSTHETIC ELBOW WITH A MOTOR-DRIVEN RELEASE MECHANISM

[75] Inventors: Woodrow Seamone, Rockville; John H. Loveless, Westminster, both of Md.

[73] Assignee: The Johns Hopkins University, Baltimore, Md.

[21] Appl. No.: 631,705

[22] Filed: Jul. 17, 1984

[51] Int. Cl.⁴ .............................................. A61F 2/58
[52] U.S. Cl. ..................................................... 623/60
[58] Field of Search ...................... 623/24, 60, 65, 59; 414/1, 4, 5, 9

[56] References Cited

U.S. PATENT DOCUMENTS

| | | | |
|---|---|---|---|
| 2,812,961 | 11/1957 | Brown et al. | 623/59 |
| 3,382,506 | 5/1968 | Collins et al. | 623/60 |
| 3,735,425 | 5/1973 | Hoshall et al. | 623/60 |
| 4,038,706 | 8/1977 | Ober et al. | 623/60 |
| 4,067,070 | 1/1978 | Seamone et al. | 623/24 |
| 4,074,367 | 2/1978 | Loveless | 623/24 |

*Primary Examiner*—Richard J. Apley
*Assistant Examiner*—James Prizant
*Attorney, Agent, or Firm*—Robert E. Archibald; Leonard W. Pojunas; Mary Louise Beall

[57] ABSTRACT

The invention concerns a releasing means for a prosthetic elbow locking mechanism. When an elbow unlocking cable is tensed by the amputee, a switch is closed, triggering a one-shot circuit. The one-shot circuit emits a single pulse which drives the motor of the prosthetic elbow, turning the motor a few degrees and lifting the arm such that any frictional engagement between an elbow locking pawl and an elbow gear is relaxed. The locking pawl is readily withdrawn from engagement with the gear, once the motor is pulsed, upon continued application of further tension to the elbow unlocking cable.

32 Claims, 4 Drawing Figures

PROSTHETIC ELBOW WITH A MOTOR-DRIVEN RELEASE MECHANISM

STATEMENT OF GOVERNMENTAL INTEREST

The Government has rights in this invention pursuant to Contract N00024-83-C-5301 awarded by the Department of the Navy.

BACKGROUND OF THE INVENTION

The invention relates to a means for releasing the locking mechanism of a prosthetic elbow. Various artificial elbows have been suggested which include a mechanism for locking the elbow in a chosen, flexed position and for releasing the locked elbow when further movement is desired. In U.S. Pat. No. 2,812,961 to Brown et al, a prosthetic locking hinge for an artificial arm is described wherein a spring biases a sliding tooth into engagement with a gear sector such that the humeral section of the arm is maintained in an angular relationship with respect to the forearm section via the now rigid hinge. Shoulder movement by the prosthesis wearer tenses a cable which disengages the tooth from the gear sector, enabling the elbow to bend to a new position. A similar mechanically operated device is disclosed in U.S. Pat. No. 3,382,506 to Collins et al, wherein a single pull-cord is utilized for unlocking the elbow joint to permit angular motion of the forearm. The elbow joint includes an arcuate toothed member which is engaged by a latch mounted in the upper arm. The pull-cord is connected via pulleys to a sliding device for engaging (or withdrawing) the latch with (or from) the toothed member. As the latch disengages, the toothed member rotates. In U.S. Pat. No. 4,038,706 to Ober et al, an elbow mechanism is shown having a control cable which rides on a first pulley in the forearm and a second pulley accommodated inside a spring-biased sliding lock, also in the forearm. An initial tension on the cable by the wearer withdraws the lock from a cut-out in the arm against the force of the biasing spring, while further tension on the cable causes the elbow to bend.

Protheses have also been proposed which include a drive motor for powered flexing or movement thereof. U.S. Pat. No. 3,735,425 to Hoshall et al discloses a myoelectrically controlled prosthesis with a closed-loop servo system comprising a sensor, amplifier, control unit and power pack. An artificial hand opens in direct proportion to control signal amplitude as the muscles of the wearer are contracted. Hoshall et al do not discuss a flexing elbow, but only address operation of a prosthetic hand via the motor. Seamone et al, in U.S. Pat. No. 4,067,070, describe a motor-driven prosthetic arm having an elbow joint lock and cable mechanism. The mechanism includes an electronic circuit which couples a solenoid to a motor. The solenoid is activated to control a radially disposed pawl member which slidably engages and disengages a toothed wheel to respectively lock and unlock the elbow. A first pulse is supplied to a lock-solenoid, whereby a ratchet wheel is locked by a pawl to prevent opening of a grasping hook assembly. Immediately following the first pull, the ratchet wheel is released and a second pulse is generated which locks the elbow, continued energization of the motor developes cable tension sufficient to open the grasping hook assembly. The elbow is unlocked when a releasing cable is tensed. A substantially similar device is disclosed in Loveless' U.S. Pat. No. 4,074,367 for a prosthetic load-lift hook locking mechanism. The pawl engages teeth of the ratchet wheel as long as there is steady tension on the cable which urges the ratchet wheel (via an integral pulley) counter clockwise. However, Loveless teaches that once the elbow is locked and the cable tension is released, a spring allows clockwise rotation of the ratchet wheel, permitting the pawl to clear the ratchet wheel teeth.

When an object is lifted with a prosthesis, the object's weight creates a downward force at the prosthesis end, generating a substantial torque at the elbow joint. If the elbow is locked in the manner of the prior art devices a locking elbow pawl is engaged with a tooth of an elbow gear. Owing to the torque generated by the lifted weight, the elbow gear tends to turn against the locking pawl such that a great frictional force is present between the locking pawl and the adjacent elbow gear tooth. When the amputee attempts to unlock the elbow joint by tensing a release cable connected to the locking pawl, the frictional force is of such magnitude that the locking pawl cannot be dislodged from the elbow gear and further bending of the elbow is prohibited.

OBJECTS AND SUMMARY OF THE INVENTION

In view of the problems inherent in the prior art devices, it is an object of the invention to provide a means for readily releasing a locked prosthetic elbow.

Another object is to present a prosthetic elbow unlocking means which is activated by a single motion of the amputee's shoulder.

A further object is to realize a simple control circuit for pulsing the standard drive motor of a prosthesis for the easy release of a locked elbow.

Included in the apparatus for releasing a locked prosthesis elbow is a spring-biased element connected to one end of a shoulder-activated release cable. Initial tension on the release cable causes the element to compress its biasing spring while a locking pawl remains stationary. An electrical contact is brushed by the element to close a switch, activating a one-shot circuit. A pulse signal is generated by a one-shot circuit to the drive motor typically present in prostheses. The drive motor begins to rotate and reel in an operating cable. In response, the prosthetic forearm lifts and the elbow gear rotates opposite to the direction of rotation urged by the prosthetic arm weight and any carried load. The rotation of the elbow gear negates the frictional engagement between the locking pawl and elbow gear tooth. Continued tensing of the release cable by the amputee causes the spring biased element to engage and lift the locking pawl from the path of the gear teeth. The drive motor is then actuated in a standard manner to vary the prosthetic elbow angle as desired.

DETAILED DESCRIPTION OF THE INVENTION

Figure 1:
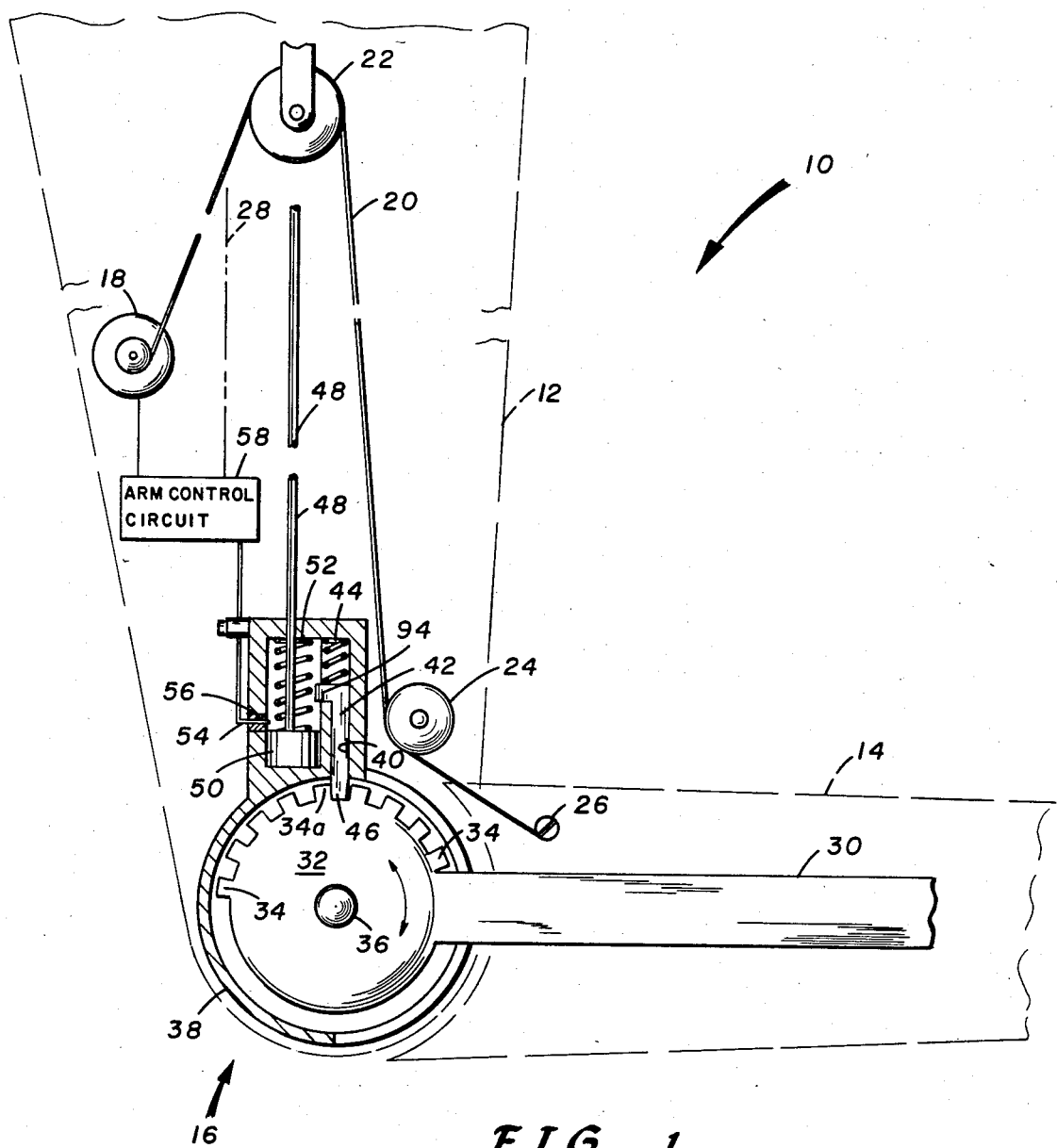
FIG. 1 shows a diagrammatic view of the invention as embodied in a prosthetic arm.

FIG. 1 shows a prosthetic arm generally at 10 having an upper arm 12 and forearm 14 connected by a mechanical elbow 16. A drive motor 18 mounted in the upper arm 12 reels and unreels an operating cable 20, over shoulder pulley 22 and elbow pulley 24. The operating cable 20 may be secured to the forearm 14 by means of a screw 26, for instance, or may be attached to a prosthetic hand in the manner described in U.S. Pat. No. 4,074,367. Application of tension to shoulder cable 28 actuates the motor 18 to reel the operating cable 20 toward the motor, the forearm 14 moving upward and bending the elbow 16. Conversely, the elbow 16 straightens as gravity pulls the released forearm 14 downward and the operating cable 20 unreels.

The forearm 14 is mounted on an extension bar 30 which is integral with a gear 32 having teeth 34. The gear is secured within the elbow 16 to rotate about shaft 36. An elbow housing 38 is provided, having a channel 40 in which an elbow locking pawl 42 slides. A biasing spring 44 urges the locking pawl 42 downward such that the tip 46 of the locking pawl 42 engages one of the teeth 34. The weight of the forearm and of any load carried by the prosthesis wearer generates a large torque about shaft 36. Owing to the generated torque, the gear 32 tends to turn clockwise, its tooth 34a pressing against the pawl tip 46. A substantial frictional force results between the tooth 34a and the pawl tip 46.

Tension applied to the release cable 48 by the prosthesis wearer pulls a preferably metallic slide element 50, suspended on the release cable 48, upward against the force of a releasing spring 52. A grounding wire 54 is shown passing through an insulated hole 56 into the elbow housing 38. As the slide element 50 moves upward, the grounding wire 54 is engaged thereby, grounding and hence triggering the operation of control circuit 58. In response to the triggering of arm control circuit 58, a pulse is generated to the drive motor 18 such that the operating cable 20 is reeled in slightly. The slight reeling of cable 20 causes the forearm 14 to lift and gear 38 to rotate counterclockwise (as viewed in FIG. 1), negating the frictional engagement between the pawl 46 and tooth 34a. Continued tension on the release cable 48 draws the slide element 50 upward into engagement with a protrusion 94 of the locking pawl 42. So engaged, the slide element 50 withdraws easily the locking pawl 42, the pawl tip 46 clearing the rotational path of the gear 32 since the friction therebetween was negated by the powered, counterclockwise rotation of gear 32.

Figure 2:
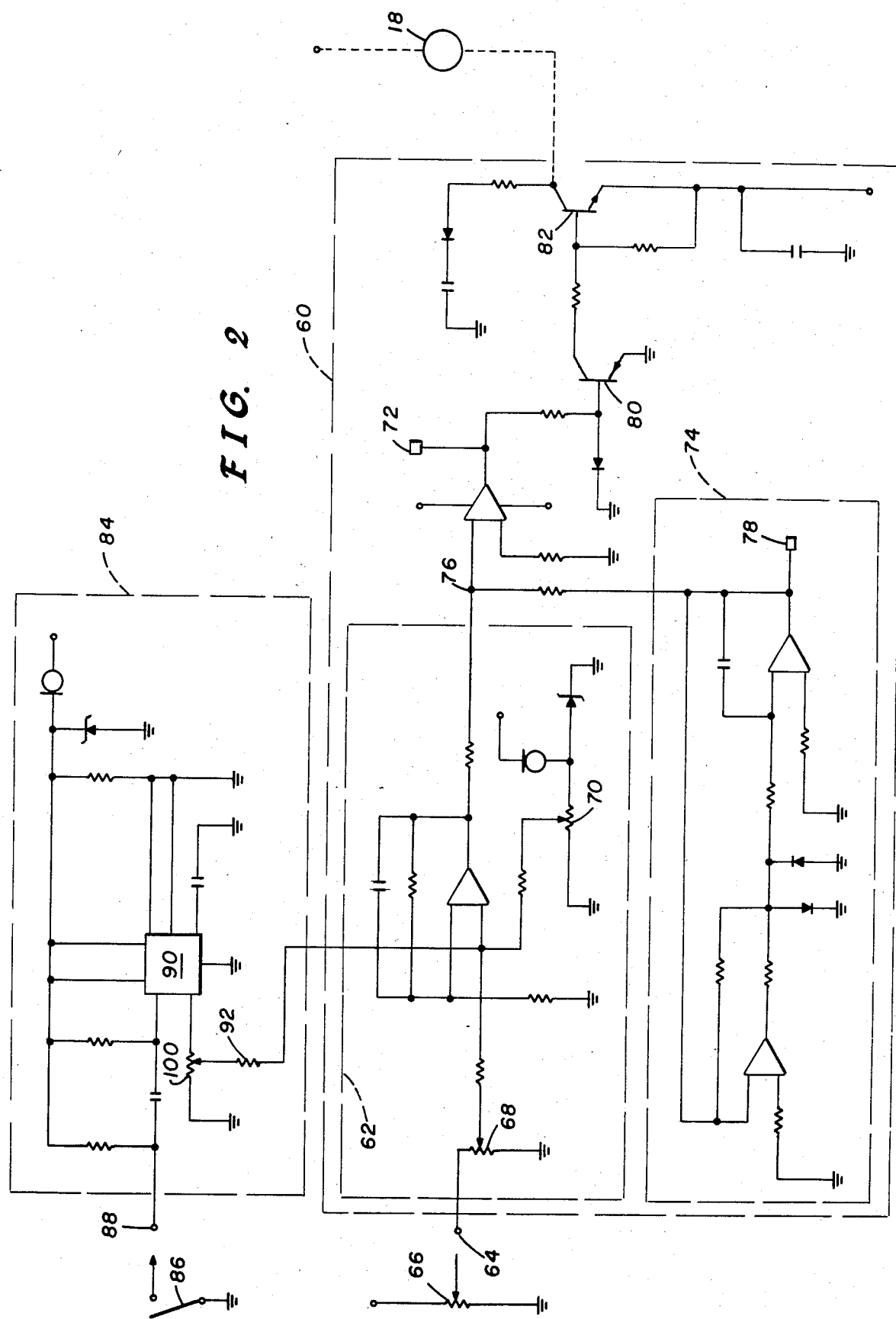
FIG. 2 shows the circuitry which controls operation of the prosthetic arm motor.

FIG. 2 reveals the components of the arm control circuit 58 of FIG. 1. Shown at 60 is a drive motor control circuit, typical of those currently used in prosthesis, and the environment for the present invention. Within the drive motor control circuit 60 is a pre-amplifier stage 62 which receives an input signal at 64 from a strain-gauge type transducer 66. The transducer 66 is connected to detect tension or movement in a second control cable (not shown), of the prosthesis. As the cable is pulled taut, a voltage is generated in response to tension in the cable. The DC voltage generated is input to the pre-amplifier stage 62 triggering the drive motor control circuit 60 for operation of the prosthesis motor 18. In the pre-amplifier stage 62 a gain potentiometer 68 is set according to the size and weight of the individual prosthesis. The bias potentiometer 70 is adjusted in a known manner so zero percent modulation occurs at test point 72.

Figure 3A:
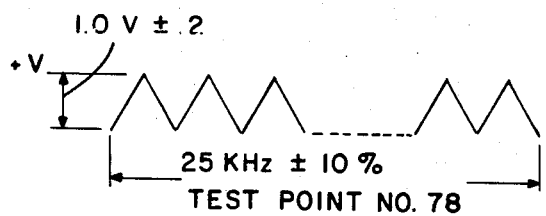
FIG. 3a shows the output of a preamplifier circuit within the FIG. 2 circuit.
Figure 3B:
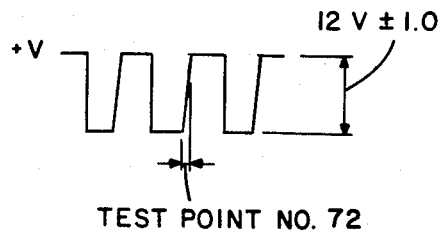
FIG. 3b shows the output of an amplifier which regulates motor operation.

An oscillator circuit 74 is also included in the drive motor control circuit 60 to provide the triangular pulsed signal at 78 shown in FIG. 3a. This triangular pulse signal is summed at 76 with the DC signal of the pre-amplifier stage 62, the scanned signal is then amplified yielding the waveform (50% modulation) of FIG. 3b at test point 78. The summed signal gates a switching transistor 80, which in turn, gates a power transistor 82 to energize the motor 18.

A one-shot circuit is shown at 84 which is triggered when the grounding wire 54 contacts the slide element 50 (see FIG. 1). A switch 86 schematically represents the contacting relationship between the grounding wire 54 and the slide element 50 contact occurring when the release cable 48 is pulled. Accordingly, the input 88 to the one-shot circuit 84 is grounded such that timer chip 90 (an ICM 7555IPA, for instance) generates a single pulse via resistor 92 to the pre-amplifier stage 62. The pulse potentiometer 100 may be adjusted as necessary to accommodate an amputee's individual needs; to compensate for the weight of the prosthetic arm, for instance. The generated pulse is summed at 76 with the triangular pulse signal from the oscillator 74 for gating the switching transistor 80. As a result, a single, modulated, full-amplitude pulse reaches and drives the motor. In turn, the gear 32 is rotated a few degrees counter clockwise and the locking pawl 42 is disengaged from the tooth 34a (see FIG. 1), allowing free movement of the prosthetic elbow.

Modifications to the proposed prosthetic elbow having a motor driven release mechanism are apparent to one skilled in the art. For instance, the one-shot circuit 84 may comprise different circuit elements, the grounding wire 54 may constitute an electrical contacting brush, and the locking pawl protrusion 94 and slide element 50 may take various complementary forms. The described embodiments are, therefore, considered to be illustrative only and not restrictive; the scope of the invention being defined by the appended claims.

What is claimed is:

1. A prosthetic arm having:
    a forearm;
    an elbow joint having a locking means and an engageable means which is engaged by the locking means to prevent bending of the elbow;
    an upper arm connected to the forearm via the elbow joint;
    a motor connected mechanically to drive the forearm relative to the upper arm about the elbow joint;
    an actuable withdrawing means connected to withdraw the locking means from engagement with the engageable means;
    a drive circuit connected electrically to the motor for regulating operation thereof;
    a switching means connected to the withdrawing means, and which is closed upon initial actuation of the withdrawing means;
    a pulsing circuit connected electrically to be triggered upon closure of the switching means and to generate a pulsed output to the motor via the drive circuit when so triggered, such that the elbow is bent slightly;
    wherein further actuation of the withdrawing means disengages the locking means from the engageable means.

2. A prosthetic arm as defined in claim 1, the pulsing circuit comprising a one-shot circuit which generates a single pulse to the motor.

3. A prosthetic arm as defined in claim 2, the withdrawing means comprising a releasing cable connected to withdraw the locking means in a first direction.

4. A prosthetic arm as defined in claim 3, the switching means comprising a slide element connected to the releasing cable, and a grounding means which is slidably engaged by the slide element when the releasing cable is actuated initially.

5. A prosthetic arm as defined in claim 4, wherein a spring is positioned adjacent the slide element to bias the slide element in a second direction opposite to the first direction.

6. A prosthetic arm as defined in claim 5, the locking means comprising an elongated pawl with a protrusion at one end and a tip portion at another end, wherein the slide element engages the protrusion to disengage the tip portion from the engageable means as the releasing cable is further actuated.

7. A prosthetic arm as defined in claim 6, the engageable means comprising a gear having at least one tooth which engages the tip portion of the elongated pawl, preventing rotation of the gear.

8. A prosthetic arm as defined in claim 7, the elbow joint comprising a housing, which encloses the gear, having a chamber in which the slide element, the spring, and the elongated pawl are positioned.

9. A prosthetic arm as defined in claim 8, the grounding means comprising a grounding wire, the housing having an insulated hole through which the grounding wire passes for engagement with the slide element.

10. A prosthetic arm as defined in claim 1, the withdrawing means comprising a releasing cable connected to withdraw the locking means in a first direction.

11. A prosthetic arm as defined in claim 10, the switching means comprising a slide element connected to the releasing cable, and a grounding means which is slidably engaged by the slide element when the releasing cable is actuated initially.

12. A prosthetic arm as defined in claim 11, wherein a spring is positioned adjacent the slide element to bias the slide element in a second direction opposite to the first direction.

13. A prosthetic arm as defined in claim 12, the locking means comprising an elongated pawl with a protrusion at one end and a tip portion at another end, wherein the slide element engages the protrusion to disengage the tip portion from the engageable means as the releasing cable is further actuated.

14. A prosthetic arm as defined in claim 13, the engageable means comprising a gear having at least one tooth which engages the tip portion of the elongated pawl, preventing rotation of the gear.

15. A prosthetic arm as defined in claim 14, the elbow joint comprising a housing, which encloses the gear, having a chamber in which the slide element, the spring, and the elongated pawl are positioned.

16. A prosthetic arm as defined in claim 15, the grounding means comprising a grounding wire, the housing having an insulated hole through which the grounding wire passes for engagement with the slide element.

17. A prosthetic arm as defined in claim 2, the locking means comprising an elongated pawl with a protrusion at one end and a tip portion at another end, wherein the withdrawing means engages the protrusion to disengage the tip portion from the engageable means as the withdrawing means is further actuated.

18. A prosthetic arm as defined in claim 17, the engageable means comprising a gear having at least one tooth which engages the tip portion of the elongated pawl, preventing rotation of the gear.

19. A prosthetic arm as defined in claim 1, the locking means comprising an elongated pawl with a protrusion at one end and a tip portion at another end, wherein the withdrawing means engages the protrusion to disengage the tip portion from the engageable means as the withdrawing means is further actuated.

20. A prosthetic arm as defined in claim 17, the engageable means comprising a gear having at least one tooth which engages the tip portion of the elongated pawl, preventing rotation of the gear.

21. A prosthetic arm as defined in claim 1, the switching means comprising a slide element connected to the withdrawing means, and a grounding means which is slidably engaged by the sliding element when the withdrawing means is actuated initially.

22. A prosthetic arm as defined in claim 21, wherein a spring is positioned adjacent the slide element to bias the slide element in a second direction opposite to the first direction.

23. A prosthetic arm as defined in claim 22, the locking means comprising an elongated pawl with a protrusion at one end and a tip portion at another end, wherein the slide element engages the protrusion to disengage the tip portion from the engageable means as the withdrawing means is further actuated.

24. A prosthetic arm as defined in claim 23, the engageable means comprising a gear having at least one tooth which engages the tip portion of the elongated pawl, preventing rotation of the gear.

25. A prosthetic arm as defined in claim 8, the elbow joint comprising a housing, which encloses the gear, having a chamber in which the slide element, the spring, and the elongated pawl are positioned.

26. A prosthetic arm as defined in claim 25, the grounding means comprising a grounding wire, the housing having an insulated hole through which the grounding wire passes for engagement with the slide element.

27. A prosthetic arm as defined in claim 2, the switching means comprising a slide element connected to the withdrawing means, and a grounding means which is slidably engaged by the sliding element when the withdrawing means is actuated initially.

28. A prosthetic arm as defined in claim 27, wherein a spring is positioned adjacent the slide element to bias the slide element in a second direction opposite to the first direction.

29. A prosthetic arm as defined in claim 28, the locking means comprising an elongated pawl with a protrusion at one end and a tip portion at another end, wherein the slide element engages the protrusion to disengage the tip portion from the engageable means as the withdrawing means is further actuated.

30. A prosthetic arm as defined in claim 29, the engageable means comprising a gear having at least one tooth which engages the tip portion of the elongated pawl, preventing rotation of the gear.

31. A prosthetic arm as defined in claim 30, the elbow joint comprising a housing, which encloses the gear, having a chamber in which the slide element, the spring, and the elongated pawl are positioned.

32. A prosthetic arm as defined in claim 31, the grounding means comprising a grounding wire, the housing having an insulated hole through which the grounding wire passes for engagement with the slide element.

* * * * *